United States Patent [19]

Müller et al.

[11] Patent Number: 5,179,077
[45] Date of Patent: Jan. 12, 1993

[54] 4-METHYL-3-PENTYL-2(5H)-FURANONE

[75] Inventors: Peter M. Müller, Therwil; Hans-Jakob Wild, Wolfhausen, both of Switzerland

[73] Assignee: Givaudan Corporation, Clifton, N.J.

[21] Appl. No.: 766,694

[22] Filed: Sep. 27, 1991

[30] Foreign Application Priority Data

Oct. 4, 1990 [CH] Switzerland ............ 3193/90

[51] Int. Cl.$^5$ .............................. A61K 7/46
[52] U.S. Cl. ................... 512/11; 549/295; 426/536
[58] Field of Search ........... 541/295, 313; 512/11; 426/536

[56] References Cited

U.S. PATENT DOCUMENTS

| 3,331,837 | 7/1967 | Lehmann | 549/295 |
| 4,257,923 | 3/1981 | Escher | 512/11 |
| 4,659,843 | 4/1987 | Binger et al. | 549/295 |
| 4,968,817 | 11/1990 | Brima | 549/295 |

FOREIGN PATENT DOCUMENTS

| 1920176 | 10/1970 | Fed. Rep. of Germany | 549/295 |
| 2-53784 | 2/1990 | Japan | 549/295 |
| 2311469 | 2/1990 | Japan | 549/295 |
| 1075456 | 8/1964 | United Kingdom | 549/313 |

OTHER PUBLICATIONS

Demnity, Tetra. Letters, vol. 30, pp. 6109–6112 (1989).
Gadge et al., Tetra Letters, vol. 50, pp. 4443–4446 (1977).
R. Edwards et al., J. Chem. Soc. Perkin Trans. 1, (3), (1979), 803.

Primary Examiner—James H. Reamer
Attorney, Agent, or Firm—Robert F. Tavares; Linda A. Vag

[57] ABSTRACT

The invention concerns the novel compound, 4-methyl-3-pentyl-2 (5H)-furanone, I, a process for the manufacture of I and fragrance and flavor compositions containing I.

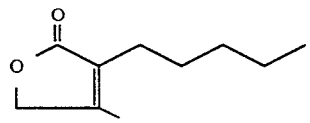

3 Claims, No Drawings

4-METHYL-3-PENTYL-2(5H)-FURANONE

SUMMARY OF THE INVENTION

The invention concerns the novel compound, 4-methyl-3-pentyl-2(5H)-furanone, I, a process for the manufacture of I and fragrance and flavor compositions containing I.

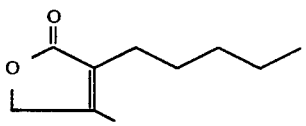

Compound I is described as having pleasant, pronounced natural flowery and fruity notes. The organoleptic properties of I make it particularly suitable for use as an odorant and/or flavorant.

DESCRIPTION OF THE PREFERRED EMBODIMENTS

Compound I is prepared by a novel process which comprises dehydrating a compound of the formula

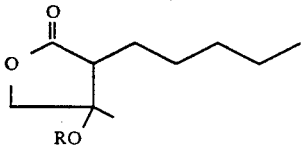

wherein R represents hydrogen or an acyl, e.g. an $C_{1-5}$-alkanoyl group. The nature of the acyl group is not critical to the invention. It depends on practical considerations such as the commercial availability of acyl, e.g. $C_{1-5}$-alkanoyl derivatives of hydroxyacetone, the latter being used as a starting material in the process used to prepare compound II as described below. The alkylcarbonyl groups, having from one to five carbon atoms, are especially suitable acyl groups with the methylcarbonyl, i.e. acetyl, being preferred due to the ready availability of acetoxyacetone.

The dehydration of compound II can be effected using protonic acids, e.g. using mineral acids such as hydrochloric acid, sulfuric acid, phosphoric acid, perchloric acid, etc. or, preferably, using organic sulfonic acids such as p-toluenesulfonic acid, etc. The dehydration can be carried out in a solvent such as a hydrocarbon, alcohol or ether and at room temperature or, preferably, at an elevated temperature.

Compound II can be prepared:

a) from an alkyl α-haloheptanoate and hydroxyacetone, or preferably, a derivative of hydroxyacetone such as an acyl, e.g. alkanoyl derivative, using Reformatzky reaction conditions, or b) from the corresponding α-halocarboxylic acid ester, i.e. heptanoic acid ester of the hydroxyacetone by way of an intramolecular Reformatzky reaction.

The compounds of formula II are novel and form a further object of the present invention.

Compound I is distinguished by pleasant, pronounced natural flowery and fruity notes. These notes are described as powerful and fresh. The side-notes which appear are coconut-like, spicy and tobacco-like. Moreover, compound I is distinguished by a high diffusion capability combined with an extraordinary adhesion. Even when used in low concentrations it intensifies and enriches the olfactory impression of odorant compositions, especially of flowery and fruity compositions or bases. Compound I combines with numerous known odorant ingredients of natural or synthetic origin, whereby the range of the natural raw materials embraces not only readily-volatile, but also moderately-volatile and difficulty-volatile components and that of the synthetics can embrace representatives from practically all classes of substances, as will be evident from the following compilation:

Natural products: Basil oil, tree moss absolute, mugwort oil, bergamot oil, cassis bud absolute, castoreum, cedarwood oil, ciste labdanum, civet, coriander oil, oak moss, elemi oil, pine needle oil, galbanum, geranium oil, clove oil, jasmin absolute and its synthetic substitute, jonquil absolute, camomile oil, labdanum, lavender oil, mandarin oil, mastix absolute, mentha citrata oil, myrrh oil, palmarosa oil, patchouli oil, petitgrain oil Paraguay, sandalwood oil, thyme oil, vassoura oil, musk infusion, styrax, birch tar, vetiver oil, franincense, ylang-ylang oil, lemon oil, civet oil, etc.

Alcohols: Citronellol, Dimetol ® (Givaudan, 2,6-dimethyl-heptan-2-ol), geraniol, cis-3-hexanol, linalool, Nonadyl ™ (Givaudan, 6,6-dimethyl-nonan-2-ol), phenylethyl alcohol, Rhodinol ™ (Givaudan, 3,7-dimethyl-oct-6-en-1-ol), Sandela ® (Givaudan, 3-isocamphyl-5-cyclohexanol), Sandalore ® (Givaudan, 3-methyl-5-(2',2',3'-trimethylcyclopenta3'-en-1'-yl)-pentan-2-ol), terpineol, etc.

Aldehydes: α-Amylcinnamaldhyde, cyclamen aldehyde, decanal, dodecanal, heliotropin, α-hexylcinnamaldehyde, hydroxy-citronellal, 4-(4-hydroxy-4-methyl-pentyl)-cyclohex-3-en-1-carboxaldehyde, 2,6,10-trimethyl-9-en-1-al, undecanal, ω-undecylene aldehyde, vanillin, etc.

Ketones: Isoraldeine ® (Givaudan, isomethyl-α-ionone), α-ionone, β-ionone, 3-phenylisocaranone, acetylated cedarwood oil, p-methylacetophenone, etc.

Esters: Ethyl acetoacetate, amyl salicylate, benzyl acetate, cedryl acetate, cinnamyl formate, citronellyl acetate, geranyl acetate, cis-3-hexenyl acetate, cis-3-hexenyl benzoate, linalyl acetate, linalyl anthranilate, methyl dihydrojasmonate, Methambrat ™ (Givaudan, 1-acetoxy-1-methyl-2-sec.-butylcyclohexane), Myraldylacetat ™ (Givaudan, 4-(4-methyl-3-pentenyl)cyclohex-3-en-1-yl-carbinyl acetate), phenoxyethyl isobutyrate, phenylethyl tiglate, styrallyl acetate, terpenyl acetate, 2,3,6,6-tetramethylcyclohex-2-ene-carboxylic acid ethyl ester, 3,6,6-trimethyl-2-ethyl-cyclohex-2-ene-carboxylic acid ethyl ester, vetivenyl acetate, ortho-tert.-butylcyclohexyl acetate, etc.

Various: Musk ambrette, coumarin, epoxycedrene, eugenol, Fixolide ® (Givaudan, 1,1,2,4,4,7-hexamethyl-6-acetyl-1,2,3,4-tetrahydronaphthalene), 1,3,4,6,7,8-hexahydro-4,6,6,7,8,8-hexamethyl-cyclopenta-γ-2-benzopyran, heliotropin, indole, indolene, isoeugenol, isobutylquinoline, 1,3-diacetoxy-nonane, musk ketone, limonene, p-menthane-8-thiol-3-one, Madrox ™ (Givaudan, 1-methyl-cyclododecyl methyl ether), methyleugenol, 12-oxahexadecanolide, γ-nonalactone, α-undecalactone, etc.

The compound of formula I can be used in wide limits which can extend in compositions, for example, from 0.1 (detergents)–30 wt. % (alcoholic solutions), without these values being, however, limiting values, as the experienced perfumer can also achieve effects with even lower concentrations or can synthesize novel complexes with even higher amounts. The preferred concentrations range between 0.1% and 25%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

Compound I can accordingly be used in the manufacture of compositions and—as the above compilation shows—using a wide range of known odorants or odorant mixtures. In the manufacture of such compositions the known odorants or odorant mixtures enumerated above can be used according to methods known to the perfumer such as e.g. from W. A. Poucher, Perfumes, Cosmetics, Soaps 2, 7th Edition, Chapman and Hall, London 1974.

The novel compound of formula I is also excellently suited for use in flavors of the widest variety of kind, but especially for the flavoring of tobacco.

As a flavorant compound I can be used, for example, for the production or improvement, intensification, enhancement or modification of (tropical) fruit flavors, e.g. apricot, peach, passionfruit, pineapple and banana flavors. However, nut, coconut, caramel, maple, tea and tobacco flavors also come into consideration. As fields of use for these flavors there come into consideration, for example, foodstuffs (yoghurt, confectionery etc.), semi-luxury consumables (tea, tobacco, etc.) and drinks (lemonade etc.).

The pronounced flavor qualities of compound I (sweet, coumarin-like, lactonic, resembling caramel; slightly fruity, fresh) enable it to be used as a flavorant in low concentrations. A suitable dosage, embraces, for example, the range of 0.1 ppm-100 ppm, preferably the range of 0.5 ppm-50 ppm, in the finished product, i.e. the flavored foodstuff, semi-luxury consumable or drink.

In the flavoring of, for example, tobacco the dosage can, however, also lie higher and can embrace a wider range, for example the range of 1 ppm to 1000 ppm, preferably 30-100 ppm.

The compound can be mixed with the ingredients used for flavoring compositions or added to such flavorings in the usual manner. Under the flavorings used in accordance with the invention there are to be understood flavoring compositions which can be diluted or distributed in edible materials in a manner known per se. They contain, for example, about 0.1-10, wt. % especially 0.5-3, wt. %. They can be converted according to methods known per se into the usual forms of use such as solutions, pastes or powders. The products can be spray-dried, vacuum-dried or lyophilized.

The known flavoring substances which are conveniently used in the manufacture of such flavorings are either already referred to in the above compilation or can be taken readily from the literature such as e.g. J. Merory, Food Flavorings, Composition, Manufacture and Use, Second Edition, The Avi Publishing Company, Inc., Westport, Conn. 1968, or G. Fenaroli, Fenroli's Handbook of Flavor Ingredients, Second Edition, Volume 2, CRC Press, Inc. Cleveland, Ohio, 1975.

For the manufacture of such usual forms of use there come into consideration, the following carrier materials, thickening agents, flavor improvers, spices and auxillary ingredients, etc.:

Gum arabic, tragacanth salts or brewers' yeast, alginates, carageen or similar absorbents; indoles, maltol, dienals, spice oleoresins, smoke flavors; cloves, diacetyl, sodium citrate; monosodium glutamate, disodium inosine-5'-monophosphate (IMP), disodium guanosine-5-phosphate (GMP); or special flavoring substances, water, ethanol, propylene glycol, glycerine, etc.

ILLUSTRATION OF THE PREFERRED EMBODIMENTS

EXAMPLE 1 a) Zinc powder (65.37 g, 1 mol) and 3.27 g (50 mmol) of iodine are placed in 400 ml of toluene. This violet suspension is heated to 80° C. in an oil bath while stirring and treated within 80 minutes with a solution of 118.55 g (500 mmol) of ethyl 2-bromoheptanoate and 87.08 g (750 mmol) of acetoxyacetone in 100 ml of toluene. The exothermic reaction which sets in immediately can be held at 80°-90° C. by removing the oil bath. After a further 90 minutes at 80° C. the reaction mixture, cooled to room temperature, is treated with 400 ml of ice-water and then with 120 ml of 20% HCl and stirred for 30 minutes. Then, it is extracted three times with 500 ml of ether in a separating funnel. The ether phases are washed with 500 ml of sat. $NaHCO_3$ solution and with 500 ml of sat. NaCl solution, dried over $MgSO_4$ and concentrated on a rotary evaporator. The crude product distills at 110°-112° C./0.06 mbar and gives 49.64 g (43.5%) of 4-acetoxy-4-methyl-3-pentyl-tetrahydrofuran-2-one.

IR (liq. film): 1780s,1740s, 1460m, 1370s, 1230s, 1025s $cm^{-1}$.

NMR ($CDCl_3$) 200 MHz: 0.9(t,3H), 1.3-1.8(m,8H), 1.54 and 1.70(2s,3H), 2.05 and 2.07(2s/3H), 2.33 and 2.78(2t/1H), 4.40 and 4.46(2q/2H) ppm.

MS (m/e): 169, 158, 89(100%), 43.

b) 4-Acetoxy-4-methyl-3-pentyl-tetrahydrofuran-2-one (125.33 g, 549 mmol) is placed with 2.61 g (13.7 mmol) of p-toluenesulphonic acid and held at 150° C. for 4 hours while stirring. The acetic acid which is cleaved off is distilled off over a Vigreux column. The reaction solution, cooled to room temperature, is diluted with 500 ml of ether and washed in a separating funnel with 2×200 ml of sat. NaCl solution. Drying of the ether phase over $MgSO_4$ and concentration on a rotary evaporator as well as distillation at 100°-103° C./0.12 mbar yields 71.34 g (77.3%) of 4-methyl-3-pentyl-2(5H)furanone.

IR (liq. film): 1750s, 1680s, 1450m, 1090s, 1040s $cm^{-1}$.

NMR ($CDCl_3$) 200 MHz: 0.9(t,3H), 1.3(m,8H), 1.6(m,2H), 2.03(s/3H), 2.25(t/2H), 4.62(m/2H) ppm.

MS (m/e): 168(M+) 153, 139, 126, 112(100%).

EXAMPLE 2 a) 2-Bromoheptanoic acid (86.0 g, 411.3 mmol) is placed in 600 ml of dimethylformamide, 49.95 g (493.6 mmol) of triethylamine are added dropwise thereto within 5 minutes at 20° C. and the pale yellow solution is stirred at room temperature for 15 minutes. Chloroacetone (57.07 g, 617 mmol) is added dropwise during 30 minutes and the yellow-brown suspension is stirred at room temperature for 90 minutes. The reaction mixture is poured on to 1 l of 1N HCl and ice and extracted in a separating funnel with 3×500 ml of ether. The organic phases are washed with 2×200 ml of water, dried over $MgSO_4$ and concentrated on a rotary evaporator. Distillation at 86°-88° C./0.05 mbar yields 80.56 g (73.9%) of acetylmethyl 2-bromoheptanoate.

IR (film): 1750s(shoulder), 1735s, 1370m, 1275m, 1145s cm$^{-1}$.

NMR (CDCl$_3$) 200 MHz: 0.9(t,3H), 1.3-1.6(m,6H), 1.9-2.2(m,2H), 2.2(s,3H), 4.34(t,1H), 4.74(q,2H) ppm.
MS (m/e): 194, 191, 185, 111, 83, 43(100%).

b) Powdered zinc (39.61 g, 606 mmol) is suspended in 500 ml of tetrahydrofuran. Then, 1.92 g (15 mmol) of iodine are added and 80.34 g (303 mmol) of acetyl-methyl 2-bromoheptanoate in 100 ml of tetrahydrofuran are added dropwise at 67° C. within 1 hour. The grey-green suspension is stirred at reflux temperature for a further 1 hour. The cooled reaction mixture is poured onto 500 ml of 1N HCl and ice and stirred for 10 minutes. It is then extracted in a separating funnel with 3×500 ml of ethyl acetate. The organic phases are dried with MgSO$_4$, concentrated on a rotary evaporator and dried in high vacuum. There are obtained 77.21 g of 4-hydroxy-4-methyl-3-pentyl-tetrahydrofuran-2-one.

IR (film): 3400m, 1750s, 1025m cm$^{-1}$.
MS (m/e): 187, 171, 169, 116, 101 (100%), 99.

c) 4-Hydroxy-4-methyl-3-pentyl-tetra-hydrofuran-2-one (77 g, 413.4 mmol) is treated with 1.57 g (8.3 mmol) of p-toluenesulphonic acid and heated at 150° C. for 2 hours, with the resulting water being distilled off over a column with a weak stream of nitrogen. The cooled reaction solution is diluted with 300 ml of ether and washed in a separating funnel 3× with 100 ml of water. The aqueous phases are back-washed with 100 ml of ether. Drying of the organic phases over MgSO$_4$, concentration on a rotary evaporator and flash distillation over a short Vigreux column at 0.3 mbar yields 44.63 g of a pale yellow liquid. By distillation on a Widmer column at 100° C./0.07 mbar there are obtained 37.73 g (54.2%) of 4-methyl-3-pentyl-2(5H)-furanone. IR, NMR and MS spectra are identical with Example 1b.

EXAMPLE 3

In compositions a), b) and c) compound I confers volume and fullness which reflect especially in the fruity and flowery aspects.

a) flowery, cosmetic accord:

| | Parts by weight | |
|---|---|---|
| I | — | 20.00 |
| Benzyl acetate | 100.00 | 100.00 |
| Geranyl acetate | 100.00 | 100.00 |
| p-t-Butylcyclohexyl acetate | 100.00 | 100.00 |
| Verdyl acetate | 20.00 | 20.00 |
| Phenylethyl alcohol | 150.00 | 150.00 |
| Hexyl cinnamaldehyde | 100.00 | 100.00 |
| Bergamot essence | 200.00 | 200.00 |
| Cyclohexylallyl propionate | 1.00 | 1.00 |
| Dimetol ® (Givaudan, 2,6-dimethylheptan-2-ol) | 20.00 | 20.00 |
| Dipropylene glycol | 30.00 | 10.00 |
| Methylphenylcarbinyl acetate | 2.00 | 2.00 |
| Isoeugenol | 2.00 | 2.00 |
| Linalool | 50.00 | 50.00 |
| Geranium oxide 10%/DIP | 5.00 | 5.00 |
| Petitgrain ess. Paraguay | 20.00 | 20.00 |
| Benzyl salicylate | 100.00 | 100.00 |
| Total | 1000.00 | 1000.00 |

Use: e.g. 2% in bases for soaps, in skin cosmetics.

b) flowery fresh accord

| | Parts by weight | |
|---|---|---|
| I | — | 30.00 |
| Benzyl acetate | 80.00 | 80.00 |
| Geranyl acetate | 150.00 | 150.00 |
| Linalyl acetate | 200.00 | 200.00 |
| p-t-Butylcyclohexyl acetate | 100.00 | 100.00 |
| 2-tert. Butylcylohexyl acetate | 80.00 | 80.00 |
| Phenylpropyl alcohol | 100.00 | 100.00 |
| Dipropylene glycol | 50.00 | 20.00 |
| Eugenol | 10.00 | 10.00 |
| Isoraldeine ® 70 P (Givaudan, isomethyl-α-ionone) | 50.00 | 50.00 |
| Lemarome ® A (Givaudan, neral-citral mixture) | 30.00 | 30.00 |
| Hexyl salicylate | 50.00 | 50.00 |
| Tetrahydrolinalool | 100.00 | 100.00 |
| Total | 1000.00 | 1000.00 |

Use: e.g. 2% in a base for shower gels.

c) flowery elegant accord:

| | Parts by weight | |
|---|---|---|
| I | — | 10.00 |
| Benzyl acetate | 100.00 | 100.00 |
| Dimethylbenzylcarbinyl acetate | 40.00 | 40.00 |
| Geranyl acetate | 30.00 | 30.00 |
| Phenylethyl alcohol | 100.00 | 100.00 |
| Bergamot reconstitution | 200.00 | 200.00 |
| α-methyl-ionone | 50.00 | 50.00 |
| Cyclohexal | 50.00 | 50.00 |
| Dipropylene glycol | 10.00 | — |
| Eugenol | 10.00 | 10.00 |
| Galaxolid ® 50 DEP (IFF, 1,3,4,6,7,8-Hexahydro-4,6,6,7,8,8-hexamethylcyclopenta-γ-2-benzopyran) | 100.00 | 100.00 |
| Gardenol TM (Givaudan, methyl phenyl carbinyl acetate | 10.00 | 10.00 |
| Geraniol extra | 60.00 | 60.00 |
| Methyl Dihydrojasmonate | 20.00 | 20.00 |
| Hydroxycitronellal | 60.00 | 60.00 |
| Methylisoeugenol | 10.00 | 10.00 |
| Benzyl salicylate | 150.00 | 150.00 |
| Total | 1000.00 | 1000.00 |

Use: e.g. 15% in 90° alcohol for eau de toilette.

d) Hazelnut flavor:

| | Parts by weight |
|---|---|
| 3,4-Dimethyl-cyclopenta-1,2-dione | 6.00 |
| Vanillin | 20.00 |
| 2-Acetyl-pyrazine | 2.00 |
| Propylene glycol | 953.00 |
| Diacetyl | 3.00 |
| Dimethyl-resorcinol | 3.00 |
| γ-Nonalactone | 1.00 |
| Benzaldehyde | 2.00 |
| Furfural | 4.00 |
| Trimethyl-pyrazine | 1.00 |
| I | 5.00 |
| Total | 1000.00 |

Dosage: e.g. 0.1% in milk drinks.

In the above hazelnut flavor the 0.5 ppm of compound I produces a creamy body and mouth-feel. It thereby intensifies especially the nut character of the flavor.

e) Chocolate flavor:

| | Parts by weight |
|---|---|
| Vanillin | 80.00 |
| Phenylacetic acid | 3.00 |
| Ethyl-vanillin | 50.00 |

|  | Parts by weight |
|---|---|
| Cocoa shell extract PG | 850.80 |
| Benzaldehyde | 0.20 |
| iso-Butyric acid | 0.50 |
| Phenylethyl alcohol | 2.00 |
| Ethylphenyl acetate | 1.50 |
| iso-Valeraldehyde | 2.00 |
| Ethyl 2-dimethyl-3,5(or 6)-pyrazine | 2.00 |
| iso-Butyraldehyde | 1.00 |
| Trimethylpyrazine | 2.00 |
| I | 5.00 |
| Total | 1000.00 |

Dosage: 0.1% in milk drinks, etc.

In the above chocolate flavor the 0.5 ppm of compound I produces body and mouth-feel; it intensifies the character of the composition.

f) Pineapple flavor:

|  | Parts by weight | |
|---|---|---|
| Ethyl valerate | 1 | 1 |
| γ-Decalactone | 1 | 1 |
| Ethyl caproate | 4 | 4 |
| Ethyl 2-methylbutyrate | 4 | 4 |
| 2-Methylbutyric acid | 5 | 5 |
| iso-Amyl acetate | 9 | 9 |
| Ethyl acetate | 10 | 10 |
| Methyl 2-methylbutyrate | 10 | 10 |
| Homofuronol 20% in PG | 15 | 15 |
| Ethyl butyrate | 16 | 16 |
| Allyl caproate | 25 | 25 |
| I | — | 5 |
| Propyleneglycol | 900 | 895 |
| Total | 1000 | 1000 |

The addition of compound I produces body, a natural juicy and fresh note, and more fullness.

g) Passionfruit flavor

|  | Parts by weight | |
|---|---|---|
| Mandarin oil | 0.500 | 0.500 |
| Phenethyl Alcohol | 0.500 | 0.500 |
| Geraniol | 0.500 | 0.500 |
| cis-3-Hexenol | 0.500 | 0.500 |
| Citral | 0.500 | 0.500 |
| α-Ionone | 0.500 | 0.500 |
| γ-Undecalactone | 1 | 1 |
| Linalool | 1 | 1 |
| α-Terpineol | 1 | 1 |
| Linalyl acetate | 1 | 1 |
| Styrallyl acetate | 2 | 2 |
| Ethyl butyrate | 4 | 4 |
| Ethyl isovalerate | 5 | 5 |
| Hexyl caproate | 14 | 14 |
| Homofuronol 20% in PG (2-ethyl-4-hydroxy-5-methyl-dihydrofuran-3(2H)-one | 20 | 20 |
| Ethyl caproate | 38 | 38 |
| Hexyl butyrate | 30 | 30 |
| I | — | 5 |
| Triethyl citrate | 80 | 75 |
| Propylene glycol | 800 | 800 |
| Total | 1000 | 1000 |

The addition of I accentuates the fresh and juicy notes, and produces fullness and body.

h) Apricot flavor:

|  | Parts by weight | |
|---|---|---|
| Hexyl acetate | 1 | 1 |
| β-Damascone 10% in PG | 1 | 1 |
| γ-Undecalactone | 2 | 2 |
| cis-3-Hexenol | 2 | 2 |
| Benzaldehyde | 3 | 3 |
| trans-2-Hexenol | 3 | 3 |
| Linalool | 5 | 5 |
| γ-Dodcalactone | 5 | 5 |
| Butyric acid | 10 | 10 |
| Ethyl acetate | 10 | 10 |
| γ-Dodecalactone | 8 | 8 |
| Ethyl propionate | 10 | 10 |
| iso-Amyl acetate | 10 | 10 |
| 2-Methylbutyric acid | 10 | 10 |
| Acetic acid | 20 | 20 |
| Homofuronol 20% in PG | 20 | 20 |
| I | — | 5 |
| Propylene glycol | 880 | 75 |
| Total | 1000 | 1000 |

The addition of I produces body, fullness, rounding-off and a more juicy, more fruity and ripe and fresh note.

We claim:

1. 4-Methyl-3-pentyl-2(5H)-furanone.

2. A fragrance composition which comprises a olfactorily effective amount of 4-methyl-3-pentyl-2(5H)-furanone and at least one other olfactorily active agent.

3. A flavor composition which comprises a flavoring effective amount of 4-methyl-3-pentyl-2(5H)-furanone and at least one other flavoring agent.

* * * * *